United States Patent [19]

Jatteau

[11] Patent Number: 4,967,735
[45] Date of Patent: Nov. 6, 1990

[54] APPARATUS FOR DESTROYING CONCRETIONS IN AN OBJECT OR AN ORGANISM

[75] Inventor: Michel R. Jatteau, Paris, France

[73] Assignee: U.S. Philips Corporation, New York, N.Y.

[21] Appl. No.: 274,526

[22] Filed: Nov. 21, 1988

[30] Foreign Application Priority Data

Nov. 24, 1987 [FR] France ................... 87 16256

[51] Int. Cl.$^5$ ............................................ A61B 17/22
[52] U.S. Cl. .................................... 128/24 A; 378/99; 358/111
[58] Field of Search ............... 128/24 A, 328, 653, 128/660.03; 358/111; 378/99

[56] References Cited

U.S. PATENT DOCUMENTS

| | | | |
|---|---|---|---|
| 4,550,419 | 10/1985 | Aichinger et al. | 378/99 |
| 4,608,979 | 9/1986 | Breidenthal et al. | 128/24 A |
| 4,639,941 | 1/1987 | Hounsfield | 358/111 |
| 4,639,943 | 1/1987 | Heinze et al. | 378/99 |
| 4,811,725 | 3/1989 | Grasser | 128/24 A |

*Primary Examiner*—Kyle L. Howell
*Assistant Examiner*—K. M. Pfaffle
*Attorney, Agent, or Firm*—William Squire

[57] ABSTRACT

An apparatus for destroying concretions in an object or an organism, has a device (300) for the emission of waves, which is arranged outside said object or organism, and for focussing these waves onto the location of concretions which are localized by means of a localization device. The localization device has a fluoroscopy assembly (100) for determining an axis $S_1L_1$ of the location of the concretion to be destroyed, and an assembly (200) for detecting photons diffused transversely of said location axis. The fluoroscopy assembly (100) has an X-ray source (101) and a diaphragm (111) as well as a system (102) for the processing of signals and the calculation of coordinates. The assembly (200) for the detection of diffused photons includes a photon detector and an electronic circuit (204) for counting, the detected scintillations.

3 Claims, 1 Drawing Sheet

APPARATUS FOR DESTROYING CONCRETIONS IN AN OBJECT OR AN ORGANISM

FIELD OF THE INVENTION

The invention relates to an apparatus for destroying concretions in an objects or an organism, comprising a device for emitting waves which is outside of the object or organism and for focussing these waves onto the location of said concretions, which location is determined by means of a localization device.

Such an apparatus, also referred to as a lithotriptor, enables notably the destruction of calculi, or lithiases, inside the human body. As is known, such lithiases are the results of the formation of various types of concretions in various organs or in their excretory ducts, most frequently these ducts are the urinary or biliary ducts.

BACKGROUND OF THE INVENTION

In lithotriptor of the type which is referred to as extracorporeal, shock waves are generated outside the patient, which waves are concentrated on the lithiases by means of a focussing device. The objects is to achieve in the vicinity of the target (in order to prevent damage to the neighbouring tissues) a pressure which suffices for fragmentation or erosion of the concretion. Therefore, the apparatus must comprise a system for exactly localizing the concretions. However, it is not only necessary to know the exact location of the concretions to be destroyed, it is also useful that their displacement, if any, under the influence of the shocks applied in the course of treatment or the movements of the organs, for example during respiration or muscular contractions of the patient, can be followed.

U.S. Pat. No. 4,617,931 describes an ultrasonic pulse apparatus for destroying calculi in which, shock waves are generated by means of an ultrasonic pulse generator comprising a spherical transducer, there is also provided an auxiliary ultrasonic generator for easy localizations of the calculus. An apparatus of this type, however, has a spatial resolution which is limited to a few milimeters because of the wavelength of the ultrasonic pulses. It may, moreover, be difficult to distinguish the echoes corresponding to the calculus itself from those which are due to other biological structures neighbouring the calculus, and a comparatively long period of time may be required for performing an analysis of neighbouring slices in order to establish the plane or planes containing the calculus.

It is to be noted that lithotriptors are known which comprise an x-ray localization system whereby, using two images taken simultaneously at two different angles by means of two flouroscopy assemblies, the position of the lithiases can be established at the intersection of two straight lines corresponding to these two angles, thus also enabling the focussing of the destructive waves. An examples of such an apparatus is described in the Patent Application WO No. 85/03631.

These lithotriptors, however, have major drawbacks. If the first fluoroscopy assembly is regarded as basic equipment enabling inter alia uralogists to perform examinations and interventions by endoscopy, the use of a similar second assembly on the one hand increases the costs of the apparatus and on the other hand forces the patient to absorb a substantial amount of radiation tubes during the entire treatment or a part thereof. The use of a single fluoroscopy assembly at two succesive angles would certainly be possible, but does not enable real-time operation. Moreover, the technique used, involving one or two fluoroscopy assemblies, leads to low contrast in the image of the calculus on the one hand because of the superposition of the images of the tissues and surrounding organs and on the other hand because of the presence of numerous scattered photons. These drawbacks are avoided by the construction in accordance with the invention.

It is an object of the invention to propose an apparatus for destroying concretions which offers, at comparatively moderate costs, an image quality and a spatial resolution better than those of the prior art.

SUMMARY OF THE INVENTION

To this end, the apparatus in accordance with the invention is characterized in that the localization device comprises a fluoroscope for determining an axis $S_1L_1$ of the location of the concretion to be destroyed and an assembly for the detection of photons diffused transversely of said location axis for the exact localization of the concretion of said axis. The fluroscope itself comprises an x-ray source with a diaphragm which is arranged in front of an x-ray tube for change-over from conventional irradiation with a full diaphragm aperture to irradiation with a reduced aperture of the slice of the object or the organism containing the concretion, or vice versa, together with a system for processing the signals and for calculating co-ordinates.

The construction of the proposed localization device mitigates the drawbacks described above. Combining the operation of the fluoroscopy assembly for localizing the axis where the concretion is situation and the operation of the detector for the transverse position enables a very satisfactory spatial resolution to be obtained. This resolution, in the order of a millimeter or even less, enables even the detection of residual fragments arising during or after the destruction of the concretion.

DESCRIPTION OF THE DRAWING

The invention will now be described in detail hereinafter, by way of example, with reference to FIG. 1 which shows the localization device of the apparatus in accordance with the invention.

DESCRIPTION OF AN EMBODIMENT

Figure 1:
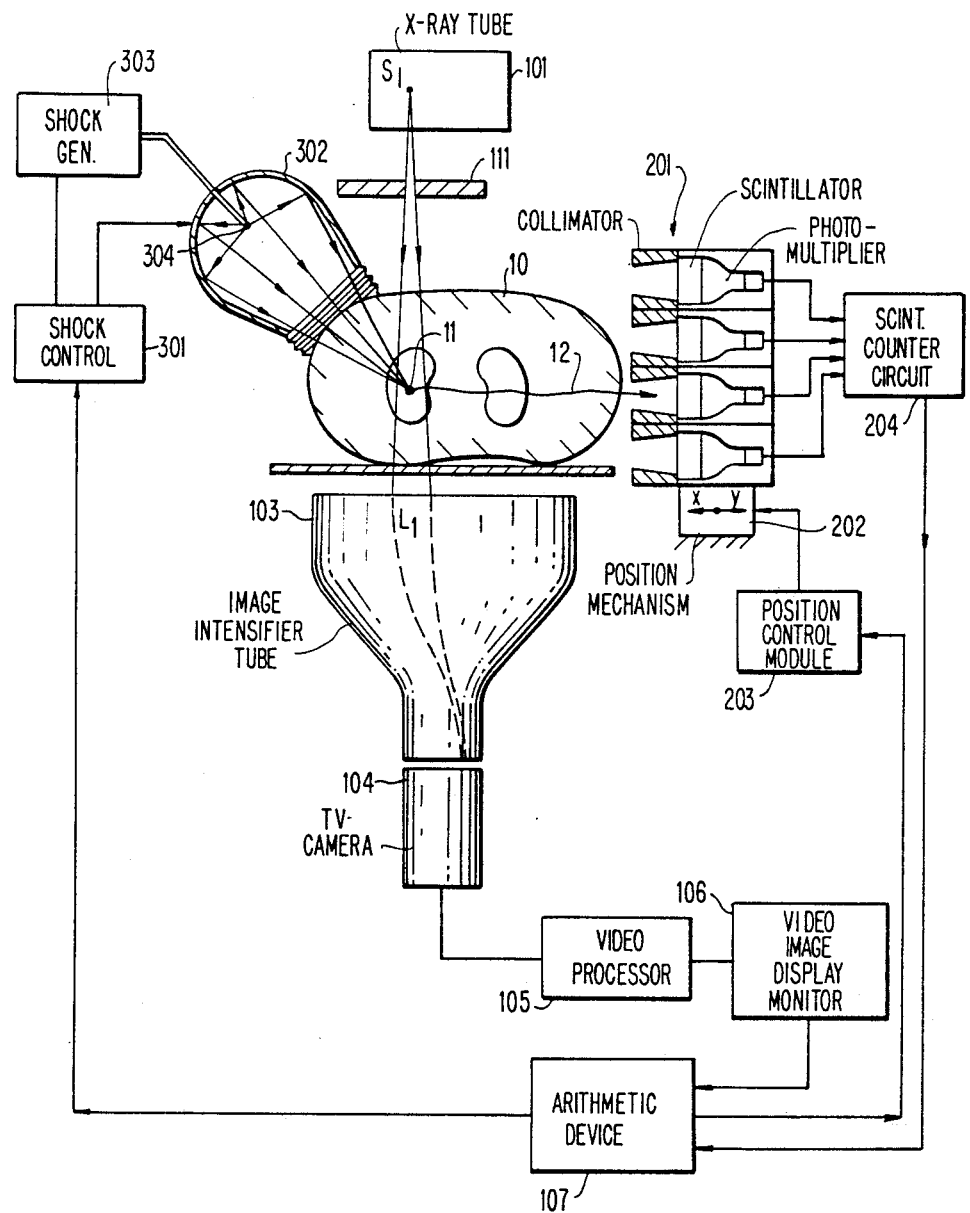

The localization device shown in FIG. 1 comprises an x-ray tube 101 a collimator diaphragm 111, and a system for processing the signals and for calculating coordinates.

The processing system is disposed on the order side of the object 10 with respect to the tube 101. It comprises, successively an image intensifier tube 103, a television camera 104, electronic processing circuits 105, an video image display monitor 106, and an arithmetic device 107. The diaphram 111 is adjustable so that alternately the whole object can be irradiated to locate the concretion and then the slice of the object 10 which contains the concretion 11 can be irradiated.

The photon detection assembly comprises an array 201 of scintillation detection probes which is finely collimated in order to detect only x-ray photons diffused in a thin slice of the object 10. This array of probes 201 is automatically oriented, by means of a linear or circular control mechanism 202, on the straight line $S_1L_1$ on which the concretion 11 to be destroyed is situated. A control module 203 is connected to the output of the arithmetic device 107 and supplies the mechanism 202 with the information concerning the position of the straight line $S_1L_1$ which is determined by the arithmetic device 107 on the basis of the video image and the position of the origin S1 of the x-ray beam.

The concretion 11 is less transparent to the x-rays than the surrounding tissued ans constitutes the source of a scattered beam 12. The exact location of this beam 12 is determined by means of one of the probes of the array 201, i.e. the probe corresponding to a maximum of photons detected. Each of these probes is formed, for example by a scintillator and a photomultiplier associated with an electronic circuit 204 for counting the scintillations and the position of the concretion 11 on the straight line $S_1L_1$ is given by the probe which supplies the highest count. The arithmetic device 107 receives on the one hand the output of the monitor 106 and on the other hand the output of the electronic circuit 204, thus delivering the three-dimensional coordinates of the concretion 11 to be destroyed, which coordinates are used to control a device for emission of destructive waves. The emission device comprises a control circuit 301 which receives the coordinates of the concretion 11 and which controls the positioning of a focussing device 302 as well as the operation of a generator 301 which is associated with a transducer 304 for generating shock waves. The focussing device 302 focuses the shock waves onto the location of the concretion 11.

It is to be noted that the invention is not restricted to the preferred embodiment described above, and that on the basis thereof many alternatives can be proposed without departing from the scope of the invention.

Such alternatives concern mainly the construction of the assembly for the detection of photons. Actually, instead of using the array of probes 201, there can be provided only a single probe for finely collimated detection which is associated with a device for mechanical scanning along the predetermined straight line $S_1L_1$. A single crystal scintillator can also be used for the detection device, which scintillator is associated with a linear array of photomultiplier tubes. The localization of the scintillations then implies a barycentric calculation (the detection device is then equivalent to a single-dimension Anger-type gamma camera).

Instead of probes with a scintillator and a photomultiplier tube use can also be made of semiconductor detection probes, for example probes of cadmium tellurium CdTe. The detector for diffused photons may also be realized on the basis of a linear scintillation detector comprising a wire chamber. Such a detector is very well suitable for the energy range of the diffused photons and offers the advantage of a high spatial resolution.

What is claimed is:

1. An apparatus for destroying a concretion in an object comprising:
   fluoroscopy means for generating a first signal manifesting an axis through said concretion to be destroyed, said fluoroscopy means comprising an x-ray source for producing an x-ray beam and adjustable diaphragm means disposed between the source and said object for selectively changing the shape of said x-ray beam in order to irradiate the object with said x-ray beam via a first enlarged diaphragm aperture of said diaphragm means in order to locate the concretion in the object and with said x-ray beam via a second reduced diaphragm aperture of said diaphragm means narrower than the first aperture in order to irradiate a first slice of the object containing the concretion, said fluoroscopy means further including image sensing means for sensing an image of the concretion produced by said flouroscopy means;
   photon detecting means for detecting photons which diffuse transversely said axis in response to irradiation of the concretion and for generating a second signal manifesting the axial position of the concretion on said axis;
   means for processing said first and second signals and for calculating the coordinate position of the concretion to generate a thrid signal manifesting said coordinate position; and
   means for emitting concretion destroying waves responsive to said third signal applied thereto and including means for focussing the waves onto said concretion at said coordinate position to destroy said concretion.

2. An apparatus as claimed in claim 1 wherein said means for processing includes means for generating a probe array positioning signal, wherein the photon detecting means comprises an array of scintillator-type detection probes, each for sensing incident diffuse transverse photons;
   collimator means for limiting detection of said transverse photons to a second slice of said object; and
   mechanical scanning means responsive to said probe array positioning signal for moving the array of probes.

3. An apparatus as claimed in any one of the claims 1 to 2, characterized in that the photon detecting means comprises one or more semiconductor detection probes.

* * * * *